United States Patent
Satherley

Patent Number: 6,142,938
Date of Patent: Nov. 7, 2000

[54] AMBULATORY DATA RECORDER HAVING ERGONOMICALLY SHAPED HOUSING

[75] Inventor: Richard J. Satherley, Felbridge, United Kingdom

[73] Assignee: Medtronic Inc., Minneapolis, Minn.

[21] Appl. No.: 09/129,917

[22] Filed: Aug. 6, 1998

[51] Int. Cl.$^7$ .................................................. A61B 5/00
[52] U.S. Cl. .................................... 600/300; 600/345
[58] Field of Search .......................... 600/300, 345–350

[56] References Cited

U.S. PATENT DOCUMENTS

| | | | |
|---|---|---|---|
| D. 396,037 | 7/1998 | Cappa et al. | D14/114.5 |
| 3,898,984 | 8/1975 | Mandel et al. | 128/2.1 A |
| 3,941,137 | 3/1976 | Vredenbregt et al. | 128/423 R |
| 4,003,379 | 1/1977 | Ellinwood, Jr. | 128/260 |
| 4,082,084 | 4/1978 | Lipscher | 128/2 D |
| 4,129,125 | 12/1978 | Lester et al. | 128/2.05 R |
| 4,183,354 | 1/1980 | Sibley et al. | 128/711 |
| 4,198,963 | 4/1980 | Barkalow et al. | 128/53 |
| 4,333,475 | 6/1982 | Moreno et al. | 128/711 |
| 4,353,375 | 10/1982 | Colburn et al. | 128/782 |
| 4,365,636 | 12/1982 | Barker | 128/716 |
| 4,370,983 | 2/1983 | Lichtenstein | 128/630 |
| 4,464,172 | 8/1984 | Lichtenstein | 604/65 |
| 4,503,859 | 3/1985 | Petty et al. | 128/635 |
| 4,529,401 | 7/1985 | Leslie et al. | 604/131 |
| 4,531,527 | 7/1985 | Reinhold, Jr. et al. | 128/696 |
| 4,592,018 | 5/1986 | Wiegman | 365/63 |
| 4,628,928 | 12/1986 | Lowell | 128/303 R |
| 4,632,119 | 12/1986 | Reichstein | 128/632 |
| 4,667,682 | 5/1987 | Ihlenfeld, III | 128/711 |
| 4,684,367 | 8/1987 | Schaffer et al. | 604/140 |
| 4,715,385 | 12/1987 | Cudahy et al. | 128/710 |
| 4,748,562 | 5/1988 | Miller et al. | 364/415 |
| 4,771,772 | 9/1988 | DeWitt | 128/303 R |
| 4,774,956 | 10/1988 | Kruse et al. | 128/635 |
| 4,794,934 | 1/1989 | Motoyama et al. | 128/734 |
| 4,895,161 | 1/1990 | Cudahy et al. | 128/710 |
| 4,900,305 | 2/1990 | Smith et al. | 604/65 |
| 4,917,092 | 4/1990 | Todd et al. | 128/421 |
| 4,974,599 | 12/1990 | Suzuki | 128/696 |
| 5,002,062 | 3/1991 | Suzuki | 128/696 |
| 5,007,427 | 4/1991 | Suzuki et al. | 128/659 |
| 5,010,888 | 4/1991 | Jadvar et al. | 128/696 |
| 5,012,411 | 4/1991 | Policastro et al. | 364/413.06 |
| 5,016,636 | 5/1991 | Kulakowski | 128/644 |
| 5,042,481 | 8/1991 | Suziki et al. | 128/639 |
| 5,072,458 | 12/1991 | Suzuki | 2/102 |
| 5,086,778 | 2/1992 | Mueller et al. | 128/696 |
| 5,107,835 | 4/1992 | Thomas | 128/419 R |
| 5,111,396 | 5/1992 | Mills et al. | 364/413.06 |
| 5,111,818 | 5/1992 | Suzuki et al. | 128/644 |
| 5,113,869 | 5/1992 | Nappholz et al. | 128/696 |
| 5,117,827 | 6/1992 | Stuebe et al. | 128/635 |
| 5,131,816 | 7/1992 | Brown et al. | 417/2 |
| 5,158,083 | 10/1992 | Sacristan et al. | 128/635 |
| 5,188,104 | 2/1993 | Wernicke et al. | 128/419 R |
| 5,213,568 | 5/1993 | Lattin et al. | 604/20 |
| 5,222,503 | 6/1993 | Ives et al. | 128/731 |
| 5,224,485 | 7/1993 | Powers et al. | 128/696 |
| 5,226,431 | 7/1993 | Bible et al. | 128/904 |
| 5,228,450 | 7/1993 | Sellers | 128/711 |

(List continued on next page.)

FOREIGN PATENT DOCUMENTS 0 356 603 9/1988 Sweden ....................... A61B 5/04

*Primary Examiner*—Robert L. Nasser
*Attorney, Agent, or Firm*—Thomas F. Woods; Michael J. Jaro; Harold Patton

[57] ABSTRACT

An ambulatory recorder having an enhanced ergonomic case is described. The case has a smooth curved semi-circular surface within a first plane along the top surface while further having an at least partially curved surface along a second end. These curved surfaces render the recorder less likely to be caught on objects or on the patient's arms or hands while worn. The recorder is thus more comfortable to wear and operate.

8 Claims, 6 Drawing Sheets

U.S. PATENT DOCUMENTS

| | | | |
|---|---|---|---|
| 5,238,001 | 8/1993 | Gallant et al. | 128/700 |
| 5,261,401 | 11/1993 | Baker et al. | 607/9 |
| 5,263,491 | 11/1993 | Thornton | 128/774 |
| 5,273,033 | 12/1993 | Hoffman | 607/46 |
| 5,292,344 | 3/1994 | Douglas | 607/40 |
| 5,305,202 | 4/1994 | Gallant et al. | 364/413.06 |
| 5,305,761 | 4/1994 | Byrne et al. | 128/697 |
| 5,307,263 | 4/1994 | Brown | 364/413.09 |
| 5,309,920 | 5/1994 | Gallant et al. | 128/710 |
| 5,338,157 | 8/1994 | Blomquist | 417/2 |
| 5,341,291 | 8/1994 | Roizen et al. | 364/413.02 |
| 5,343,870 | 9/1994 | Gallant et al. | 128/711 |
| 5,355,892 | 10/1994 | Saltzstein | 128/710 |
| 5,368,562 | 11/1994 | Blomquist et al. | 604/65 |
| 5,381,351 | 1/1995 | Kwong et al. | 364/571.04 |
| 5,388,587 | 2/1995 | Knutsson et al. | 128/741 |
| 5,411,022 | 5/1995 | McCue et al. | 128/632 |
| 5,429,602 | 7/1995 | Hauser | 604/65 |
| 5,431,634 | 7/1995 | Brown | 604/513 |
| 5,432,698 | 7/1995 | Fujita | 364/413.02 |
| 5,438,985 | 8/1995 | Essen-Moller | 600/800 |
| 5,479,019 | 12/1995 | Gross | 250/345 |
| 5,479,935 | 1/1996 | Essen-Moller | 128/734 |
| 5,507,904 | 4/1996 | Fisher et al. | 156/252 |
| 5,526,809 | 6/1996 | Fiddian-Green | 128/632 |
| 5,545,183 | 8/1996 | Altman | 607/5 |
| 5,607,460 | 3/1997 | Kroll | 607/30 |
| 5,645,068 | 7/1997 | Mezack et al. | 128/670 |
| 5,657,759 | 8/1997 | Essen-Moller | 128/654 |
| 5,670,944 | 9/1997 | Myllymaki | 128/903 |
| 5,701,894 | 12/1997 | Cherry et al. | 128/630 |
| 5,704,368 | 1/1998 | Asano et al. | 128/733 |
| 5,704,890 | 1/1998 | Bliss et al. | 600/1 |
| 5,749,907 | 5/1998 | Mann | 607/27 |

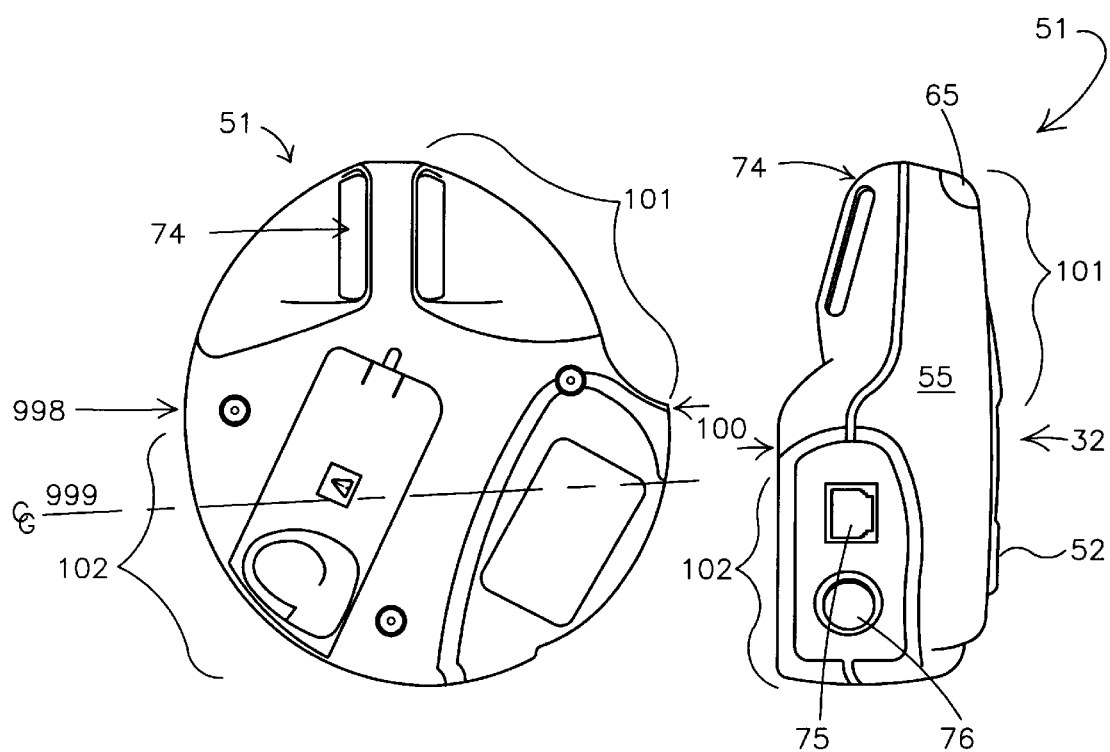
FIG. 5  FIG. 6

AMBULATORY DATA RECORDER HAVING ERGONOMICALLY SHAPED HOUSING

FIELD OF THE INVENTION

The present invention relates to ambulatory recording, for medical and especially for diagnostic purposes, by means of a portable recorder, including providing the recorder with an enhanced ergonomic case.

Ambulatory recording and recorders are widely used. Such devices include the Digitrapper Mk III™ ambulatory recorder (shown in FIGS A and B) from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram) data, EEG data (Electroencephalogram) and pH or pressure data (Motility) in the gastrointestinal tract. Preferably such a recorder should be able to record among a programmable number of channels at a variety of programmable frequencies.

One problem often faced with designing ambulatory recorders lies in the fact that the devices are ambulatory, and are carried by patients when in use. As such they must be both rugged and comfortable to use.

Among the problems with currently available recorders, however, is their shape. Ambulatory recorders are carried by patients when in use. As such they must be rugged. In addition, the recorders typically require the ability for data to be input. This data is typically input by both the physician, while the recorder is in the physician's office, and the patient, and further by the patient, while the recorder is worn. Moreover, physicians or health care faciitlties typically own several recorders, and thus the ability to stack the recorders for storage is desired.

For these reasons recorders have typically been fashioned in a boxy, cube-like configuration. For example, the Digitrapper Mk III™ ambulatory recorder from Synectics Medical AB (depicted in FIGS. A and B), the GastroScan II™ from Medical Instruments Corporation, and the SuperLogger™ from Sandhill Scientific all are essentially elongated cubes, having generally at least four if not six sides which are merely flat planes. The corners therefore also feature a variety of right angle edges.

While such designs have been highly suitable for a recorder while it is resting in the physician's office, such shapes are problematic for the patient. The right angle edges may sometimes be painful to strike, and further the flat surfaces tend to absorb the force of any object which strikes it, rather than deflecting the force.

Thus there is a need for a recorder which has an enhanced, more ergonomiclly shaped housing. In particular there is a need for a recorder which has a housing which has a majority of smooth rounded edges to permit the device to be worn and carried with a minimum of cathching on objects or absorbing shoc. The housing, however, should still permit the recorder to be place on a flat surface and acheive a stable position.

SUMMARY OF THE INVENTION

An ambulatory recorder having an enhanced ergonomic case or housing is described. The housing generally is highly rounded and feature few sharp edges. The top portion of the device is highly rounded, therby minimizing the patient's arms or fingers form catching on therecorder while being worn. The lower portion is also rounded, albeit less than the top portion. The back portion of the recorder defines a flat plane, permitting the recorder to be placed on a table top and have data entered through the keypad without the recorder rocking back and forth. The front portion of the recorder is also rounded. Finally, the recorder is further battery operated, the batteryies positioned at a point such that the center of gravity of the batteries is below the mid-line of the recorder housing when the recorder is worn. Such weight distribution tends to be felt in a more desirable manner by the patients.

BRIEF DESCRIPTION OF THE DRAWINGS

FIGS. A and B depict the prior art Digitrapper Mk III™ ambulatory recorder from Synectics Medical AB.

FIG. 5 is a back view of the recorder.

FIG. 6 is a side view of recorder 51.

The figures are not necessarily to scale.

DETAILED DESCRIPTION OF THE DRAWINGS

Figure 1A:
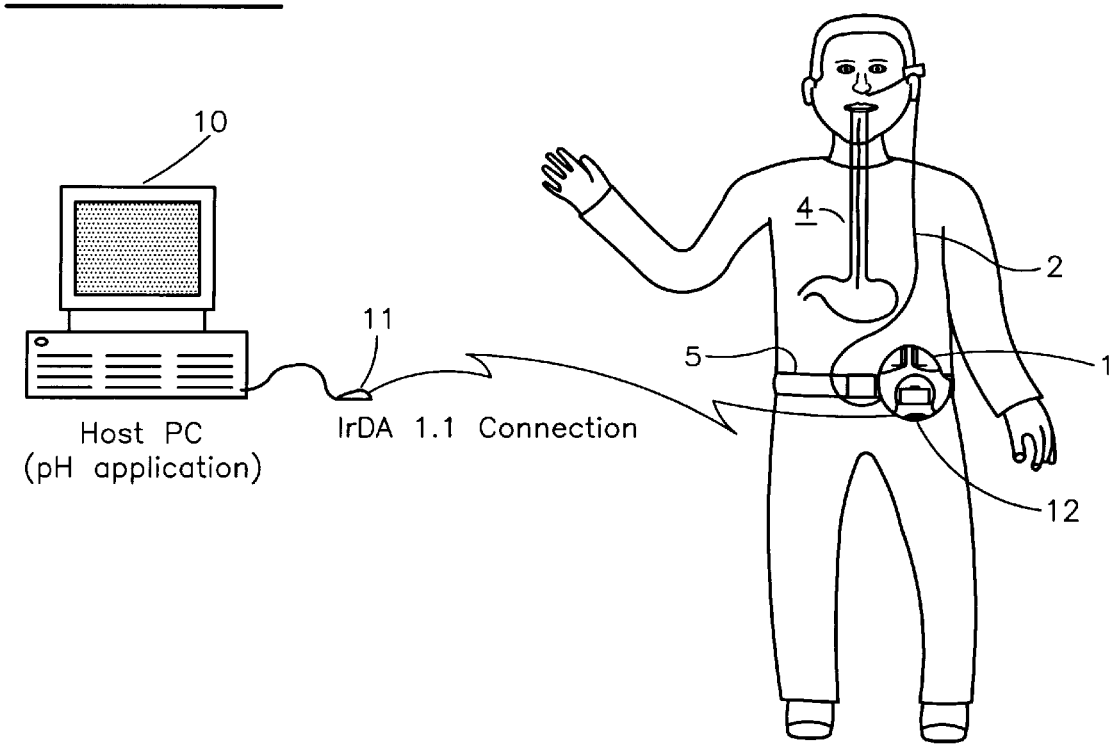
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back of the recorder enclosure which fastens to a patient's belt 5, or the same mounting may be coupled to be carried using a shoulder harness (not shown). Recorder 1 is coupled to the patient 4 through one or more sensing catheters 2. Sensing catheters may be positioned in any area of the patient's body from which data is to be sensed, including the esophagus, as depicted in. It should be noted the ambulatory recorder of the present invention may be used to collect many or various types of data including gastrointestinal (including pH and pressure) data, neurological data, as well as neuromuscular data, EEG data or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Ut. disposable 24 pH catheter Model series G91-6 or G 91-7. While a single catheter 2 is shown depicted in this figure, recorder 1 further permits two separate sensors to be coupled to the device, as seen in FIG. 1B.

As further seen in this figure, the recorder may also communicate with a host PC 10 via an infra red data link facility through an IrDA connection 11 such as, for example, a JETEYE ESI-57680 available form Extended Systems, Inc., Boise, Id., which communicates with the recorder using the infra Red Data Association 1.1 Connection Protocol. As seen, infra red data connection makes a link to infra red port 12 on recorder 1.

Figure 1B:
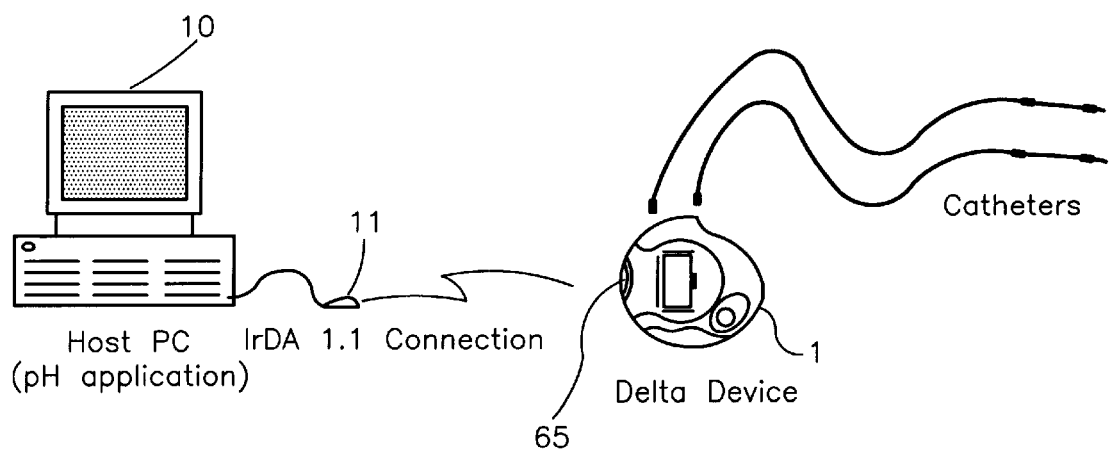
FIG. 1B illustrates a further manner in which recorder 1 may also have an infra red data communication link established with a host PC.

FIG. 1B illustrates a further manner in which recorder 1 may also have an infra red data communication link established with a host PC. In particular, infra red data communication may be further established when the recorder is not worn by the patient. As discussed in more detail below, one of the advantages of the present invention is that the infra red data components and recorder case permit such a link to be made when the device is worn as shown in FIG. 1A, as well as when the device is removed from the patient and positioned in proximity to mouse 11.

Figure 2:
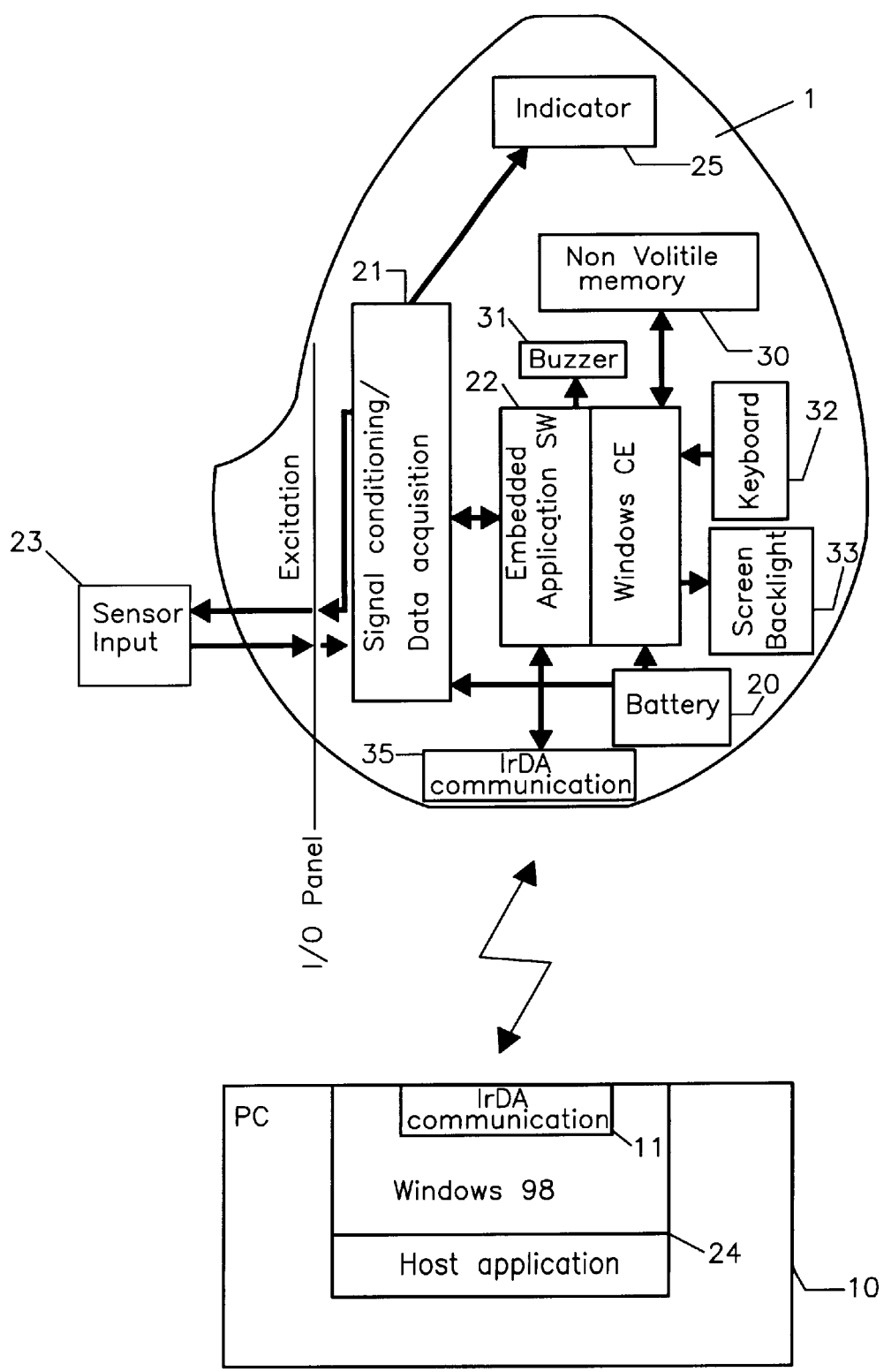
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21. The battery is coupled as well as to a non-real time processor 22 that runs the application. In the preferred embodiment battery 20 is provided by a pair of "AA"-type batteries. As disclosed in more detail below, real time processor 21 is a low power processor which is used to sample data received from sensor input 23 by a sensor attached thereto (not shown in FIG. 2).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, the second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder 1 features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In a preferred embodiment of the present invention the real time processor 21 is a model PIC16LC67IC from Microchip Technology Inc., Chandler, Ariz.; the non-real time processor 22 is a model ElanSC400IC from Advanced Micro Devices, Inc. Sunnyvale, Calif. and non-volatile memory 30a model Minicard AMMCL004AWP from Advanced Micro Devices, Inc. Sunnyvale, Calif.

Figure 3:
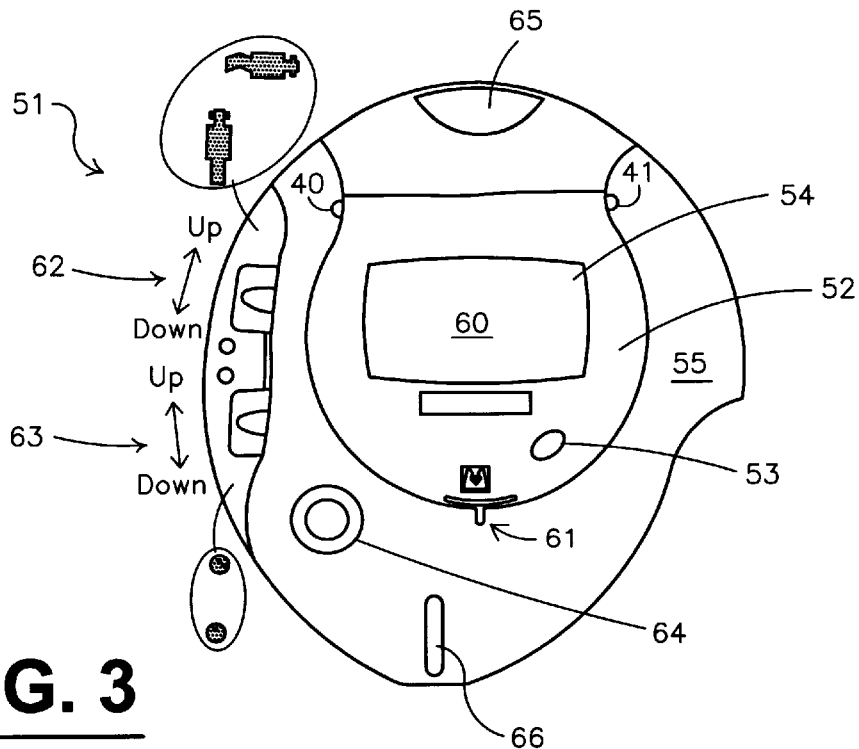
FIG. 3 is a front view of recorder according to the present invention.

FIG. 3 is a front view of recorder according to the present invention. In this view, recorder 51 has its movable front cover 52 closed. As discussed in more detail below, front cover further includes a movable push button shield 53 which allows access to one of the push button controls covered by the cover while in the down position. Shield 53, although allowing access to the push button controls, obscures any notation of the push button controls from the viewer when the cover is closed such that a very simplified control interface is presented to any user when the cover 52 is closed. Cover 52 also features a transparent window 54 to permit viewing of the LCD screen 60 which is integral with recorder (further depicted in FIG. 2). As mentioned, cover may be moved from a closed position, shown in this figure, to an open position, shown in FIG. 4. Movement is controlled by a cover catch 61, described in more detail in FIG. 9.

As seen, recorder 1 also features a pair of period switches 62 and 63 which are movable in a linear fashion from a first to a second position. In the preferred embodiment, period switch 62 is a body position switch, and the up position is used to mark periods when the patient is lying down or in a supine position. The down position is used to mark periods when the patient is standing or sitting upright. Period switch 63 preferably is a meal switch and the up position is used to mark a meal period while the down position is used for periods when the patient is not eating. The device further features, an event button 64 which the patient presses to mark events. Such events may include heart palpitations or reflux. Clock button 53, period switches 62 and 63 and event button 64 are all coupled to the keyboard function 32, shown in FIG. 2.

The device further features an infra red data output port having a two plane infra red lens 65. This feature is coupled to the infra red communication block 35 depicted in FIG. 2 and permits the device to communicate, through an infra red connection, to a host PC. The device also features an operation indicator light 66 which would indicate device operation.

Figure 4:
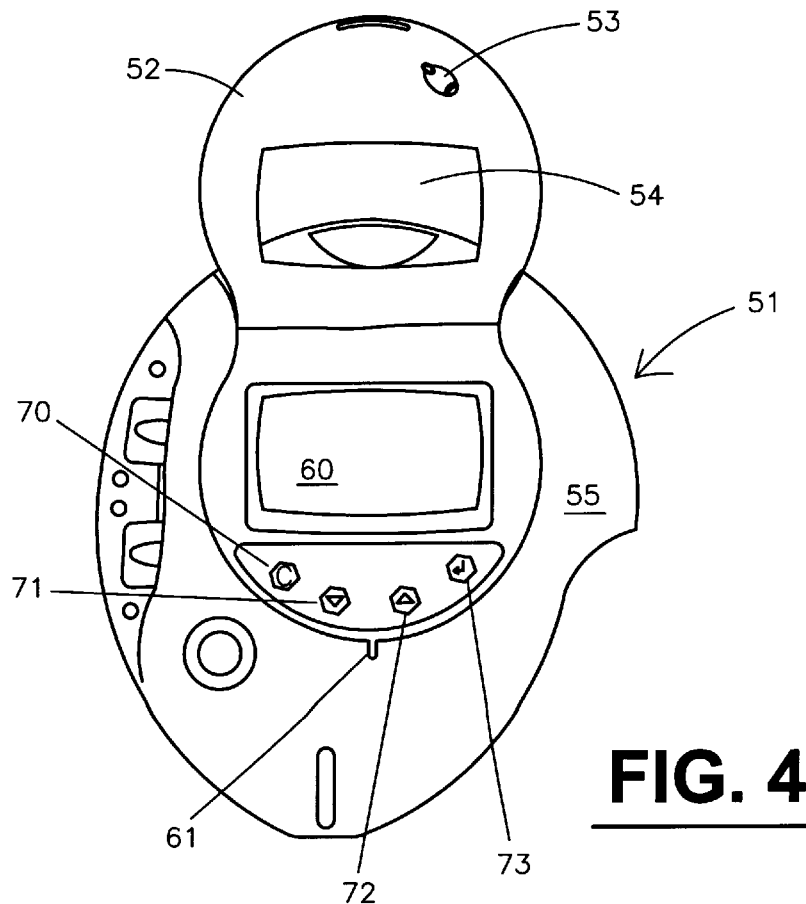
FIG. 4 is a front view of the recorder 51 in which the cover 52 has been raised.

FIG. 4 is a front view of the recorder 51 in which the cover 52 has been raised and the device is open. As seen, when open, a series of controls 70, 71, 72 and 73 are exposed. Control 70 is a push button and features, at its front face, the mark C. This control permits the user to return to the previous screen shown on display 60 without having to save any changes. Control 71 is a push button which, in the preferred embodiment, moves the selection bar shown in 60 to the next item down. Control 72 is a push button which, in the preferred embodiment, moves the selection bar to the next item up. Control 73 is, preferably, a push button which executes the current selection in the preferred embodiment.

As seen by a comparison of FIG. 3 and FIG. 4, control push button 73 may be operated regardless of whether the cover is opened or closed during the provision of movable push button 53. An important feature of this shield, however, is that it presents a different notation for the push button when the cover is closed as compared to when the cover is open. As discussed above, past ambulatory recorders have performed less than satisfactorily because too many controls were presented to the patient. While such controls are necessary to be presented to the physician so that the device may be programmed and its operating parameters set in an acceptable manner, such controls are not necessary for the patient when the device is merely recording. Thus, the movable push button shield, mounted to the movable cover, permits the device to provide an enhanced control feature set to a physician while limiting the control feature set for the patient. Cover movement is further controlled by the open cover catch 61 which permits the cover to be opened only with a tool, which in the preferred embodiment is a pen tip. Although not shown in this figure, another feature important to the device operation is that of the hinge point on which the cover is mounted. In the preferred embodiment, the hinge is functionally a break-away hinge such that if excessive force (e.g. greater than eight pounds) is provided to the cover when open it will release from its hinge points without breaking such that it may thereafter be reinserted into its hinge. The breakaway feature is provided in a known manner, such as a deformable polymer cover along with removable hinges, e.g. interlocking hemispherical hinge points and recesses. The break-away hinge is provided through the engagement of a pair of oppositely disposed pins 90 and 91 (shown here as a dotted line) integral with cover 52 which engage into enclosure 55 and, thus, permit cover to be rotated from an open to a close position and vice versa. Break-away capability is provided because the pins are of limited dimension such that they can, upon sufficient force, be moved out of the corresponding recesses and enclosure and, thus, permit cover 52 to break-away or release without further damage.

FIG. 5 is a back view of the recorder. As seen, recorder 51 features a belt loop 74 which may be used to mount the recorder to a patient using either the patient's belt or the shoulder strap. As also seen in this view, the device further features a unique weight distribution, particularly involving the device's batteries. As seen, the center of gravity 999 of the recorder taken within the major plane with the battery inserted is located below the widest portion of the recorder, generally designated as 998. This distribution of the weight below the case widest portion ensure the recorder hangs in a stable manner when worn. As best seen in FIG. 5 and also FIG. 6, the top portion 101 of the recorder is highly rounded, therby minimizing the patient's arms or fingers from catching on recorder 1 while being worn. As can be seen, the device has a partially elliptical cross section, and sectioned accross its features an at least partially elliptical cross section. The lower portion 102 is also rounded, albeit less than the top portion 101.

FIG. 6 is a side view of recorder 51. As further seen in this view, housing 55 features a pair of sensor inputs 75 and 76. In the preferred embodiment, input 75 is for a pH catheter while input 76 is for a pressure measuring catheter. As best seen in this view the back portion of the recorder defines a flat plane 100 which corresponds and is opposite to the control keypad 32 positioned beneath and covered by cover 52. Because plane 100 is flat and is directly opposite the key pad, the recorder may to be placed on a table top and have data entered through the keypad without the recorder rocking back and forth. The front portion of the recorder is also rounded. As further seen, recorder features an infra red lens 65 which permits an infrared link to a host be made using the IrD communication components shown in FIG. 2. As seen in this view, lens 65 is positioned along both an upper as well as a side surface of the recorder enclosure. This two sided or multi plane lens thereby permits a large degree of exposure to the internal IrD components inside the enclosure and thus permits an IrD link to be made with the recorder in a variety of positions relative to the IrDA communication device 11 (referring to FIG. 1A and 1B). Lens 65 may be made of an known standard lens material. In the preferred embodiment lens 65 is made of polycarbonate and the enclosure itself, including the cover, is fashioned from the polymer Crastin™ XMB 850 FR available from E.I. Du Pont De Nemours And Company, Wilmington, Del. The lens, however, should be formed so as to reach across both the upper side as well as front side of the recorder (referring once again to FIG. 6).

Figure 7:
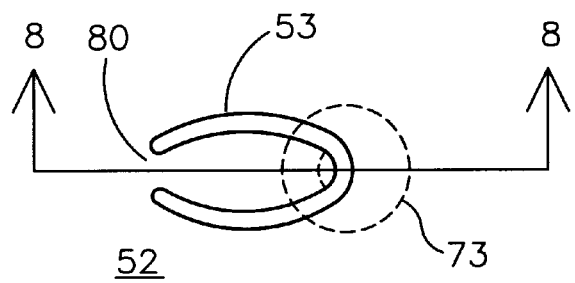
FIG. 7 is a detailed view of the movable push button shield.

FIG. 7 is a detailed view of the movable push button shield. As seen, movable push button shield 53 is designed to be positioned proximate the push button control 73, shown here as a dotted line. Shield 53 is provided by cutting away the elongated section of cover such that a cantilevered strip remains. As seen, in the preferred embodiment, the cantilever strip is somewhat oval in shape, although many or various types of shapes may also be used. The partial cutting away leaves the cantilever strip as a flexible hinge portion generally depicted here as 80 and permits the cantilever strip to open and thus be used to actuate push button.

Figure 8:
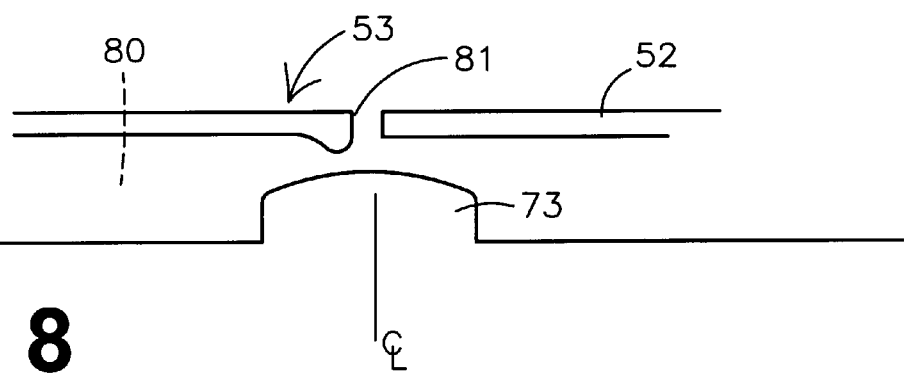
FIG. 8 is a sectional view of FIG. 7.

FIG. 8 is a sectional view of FIG. 7. As seen, the cantilever section, and the hinge which provides flexibility, are disposed generally off-center from push button 73 such that the distal end of cantilever section 81 is shown in alignment with the center line of push button 73. The distal end further features a pronounced footing to further assist in the engagement of shield 53 with push button and thus facilitate push button operation.

Figure 9:
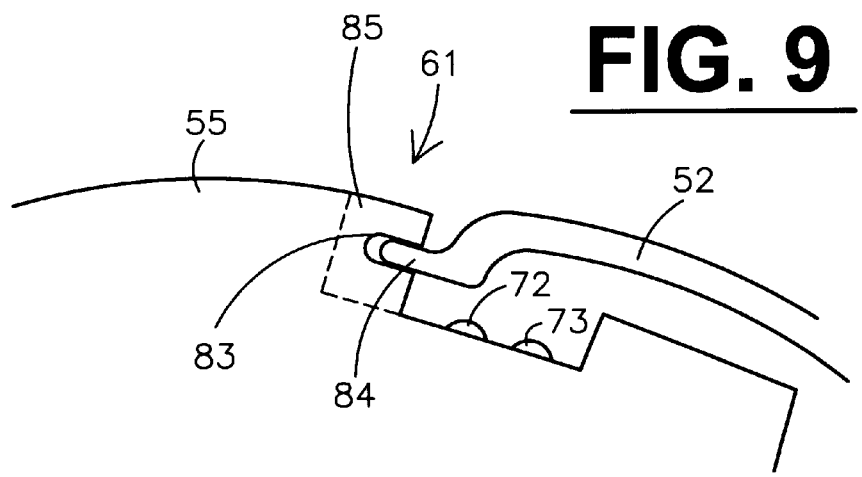
FIG. 9 is a detailed sectional view of catch.
Figure 10:
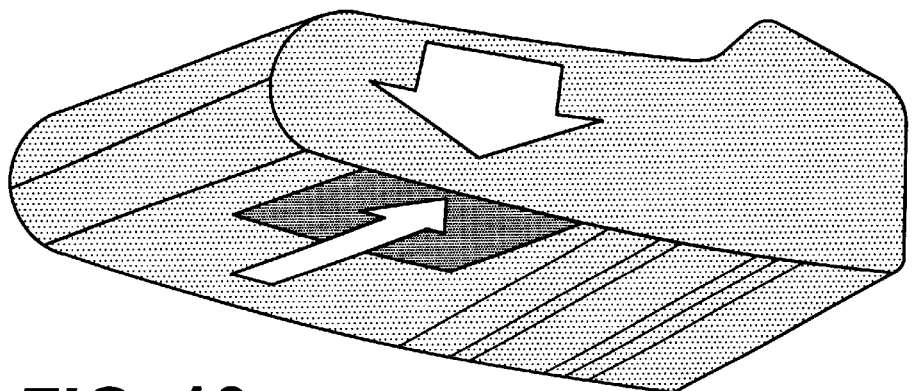
FIGS. 10 and 11 depict the prior art Digitrapper Mk III™ ambulatory recorder from Synectics Medical AB.
Figure 11:
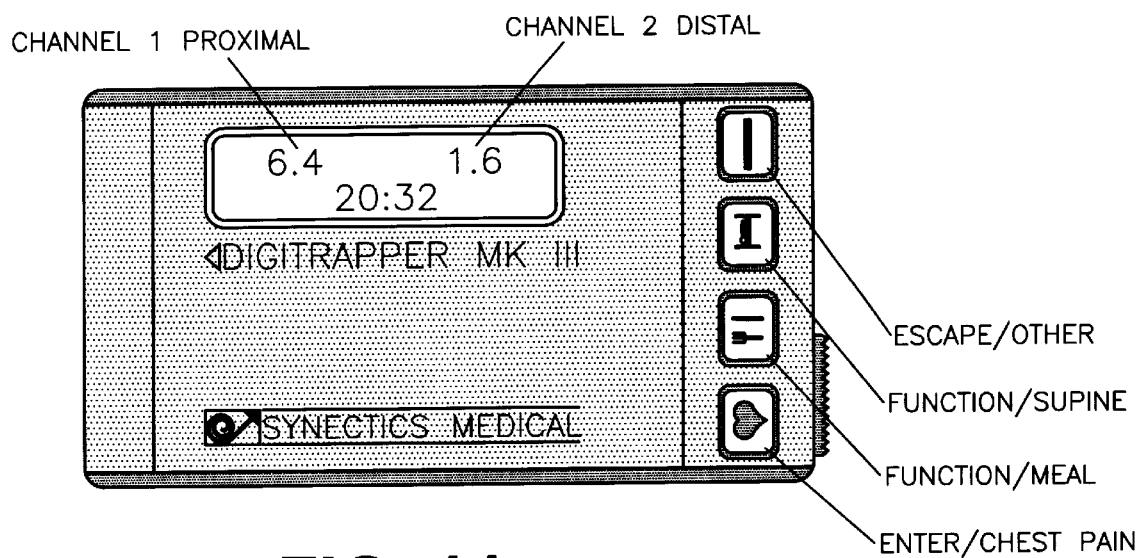

FIG. 9 is a detailed sectional view of catch 61. As discussed above, the cover may be only opened or closed through the release of catch 61. As seen, catch 61 features a recess 83 which co-operates with a finger 84 provided on cover 52. Because the cover is flexible, however, it may be deformed enough to disengage finger from recess. As further seen in this FIG. 9 and also in FIG. 3, a trench 85 is provided in housing 55 to permit the engagement and, thus, removal of tongue from recess.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory data recorder, comprising:
   a housing;
   a catheter for sensing at least one physiologic signal;
   means for connecting to the catheter disposed in the housing, the catheter connecting means connecting to at least a portion of the catheter and providing electrical and mechanical connection thereto;
   means for recording the physiologic signal disposed in the housing, the physiologic signal recording means being electrically coupled to the catheter connecting means such that the at least one physiologic signal sensed by the catheter may be recorded by the physiologic signal recording means;
   wherein the housing is ergonomically-shaped and comprises top and bottom surfaces bounded and separated by opposing first and second side edges and opposing upper and lower edges, the first and second side edges defining respective widths of the top and bottom surfaces, the widths varying substantially equally between the first and second side edges when proceeding from the lower edge to the upper edge, the upper and lower edges being separated by a minimum distance, there being a first point at which a maximum width is defined along the minimum distance, the top surface having a substantially rounded and smooth surface, the top surface, the bottom surface, the first edge, the second edge, the upper edge and the lower edge defining substantially smooth corners in regions where the surfaces intersect, the data recorder having a center of gravity disposed at a second point which lies between the lower edge and the first point.

2. An ambulatory recorder according to claim 1, wherein the bottom surface is at least partially curved.

3. An ambulatory recorder according to claim 1, wherein the physiologic signal recording means is powered by a battery.

4. An ambulatory recorder according to claim 1, further comprising an enclosure for enclosing the catheter connection means and the physiologic signal recording means, the enclosure having a first cross sectional shape when taken along a first plane which is at least partially elliptical along a first end.

5. An ambulatory recorder according to claim 4, wherein the first cross sectional shape is at least partially curved along a second end.

6. An ambulatory recorder according to claim 4, wherein the first cross sectional shape is taken along a major longitudinal plane.

7. An ambulatory recorder according to claim 4, wherein the enclosure further comprises a second cross section along a second minor longitudinal plane, the second cross section having a first end and a second end, the first end being curved.

8. An ambulatory recorder according to claim 1, wherein the physiologic signal recording means further comprises a memory.

* * * * *